US006489472B2

(12) United States Patent
Giandomenico et al.

(10) Patent No.: US 6,489,472 B2
(45) Date of Patent: Dec. 3, 2002

(54) PROCESS FOR PREPARATION OF N-1 PROTECTED N RING NITROGEN CONTAINING CYCLIC POLYAMINES AND PRODUCTS THEREOF

(75) Inventors: Christen M. Giandomenico, Blaine, WA (US); Wen Yang, Langley (CA)

(73) Assignee: AnorMED, Inc., Langley (CA)

( * ) Notice: Subject to any disclaimer, the term of this patent is extended or adjusted under 35 U.S.C. 154(b) by 0 days.

(21) Appl. No.: 09/970,288

(22) Filed: Sep. 28, 2001

(65) Prior Publication Data

US 2002/0058807 A1 May 16, 2002

Related U.S. Application Data

(60) Provisional application No. 60/237,002, filed on Sep. 29, 2000.

(51) Int. Cl.[7] .................. C07D 255/02; C07D 257/02
(52) U.S. Cl. ........................................................ 540/474
(58) Field of Search ............................................ 540/474

(56) References Cited

U.S. PATENT DOCUMENTS

| 4,885,363 A | 12/1989 | Tweedle et al. ............. 540/465 |
| 4,943,679 A | 7/1990 | Aviron-Violet et al. ...... 562/561 |
| 5,021,409 A | 6/1991 | Murrer et al. ............... 514/183 |
| 5,047,527 A | 9/1991 | Handel et al. .............. 540/474 |
| 5,064,956 A | 11/1991 | Kruper, Jr. ................. 540/474 |
| 5,132,409 A | 7/1992 | Felder et al. ................. 534/10 |
| 5,277,895 A | 1/1994 | Platzek et al. ................. 424/9 |
| 5,410,043 A | 4/1995 | Platzek et al. .............. 540/465 |
| 5,583,131 A | 12/1996 | Bridger et al. .............. 514/183 |
| 5,606,053 A | 2/1997 | Prashad et al. ............. 540/474 |
| 5,698,546 A | 12/1997 | Bridger et al. .............. 514/183 |
| 5,705,637 A | 1/1998 | Schultze et al. ............ 540/474 |
| 5,705,689 A * | 1/1998 | Lee et al. .................... 562/873 |
| 5,801,281 A | 9/1998 | Xu et al. ....................... 564/82 |
| 5,871,709 A | 2/1999 | Gries et al. ................. 424/1.65 |
| 5,919,431 A | 7/1999 | Higler et al. .............. 424/9.363 |
| 5,994,536 A | 11/1999 | Petrov et al. ............... 540/474 |
| 6,001,826 A | 12/1999 | Murrer et al. .............. 514/183 |
| 6,080,785 A | 6/2000 | Platzek et al. .............. 514/547 |

FOREIGN PATENT DOCUMENTS

WO          WO 00/45814          8/2000

OTHER PUBLICATIONS

Mir et al. (J. Org. Chem. (1994), 59(1), 173–7). Abstract.*
Bridger et al., J. Med. Chem. (1995) 38(2):366–378.
Guillaume and Marshall, Synthetic Communications (1998) 28(15):2903–2906.
O'Sullivan et al., Tetrahedron Letters (1995) 36(20):3451–3452.
Xu et al., Tetrahedron Letters (1995) 36(41):7357–7360.

* cited by examiner

*Primary Examiner*—Bruck Kifle
(74) *Attorney, Agent, or Firm*—Morrison & Foerster LLP (57) ABSTRACT

Cyclic polyamines containing N nitrogens on the ring are protected with high yields in a N-1 manner, e.g. all protected but one amino group, by using certain fluoro-containing agents that offer easy deprotection. Preferably, a new process for preparing 1,1'-[1,4-phenylenebis(methylene)]-bis1,4,8,11-tetraazacyclotetradecane is disclosed.

45 Claims, 3 Drawing Sheets

Figure 1. 13C NMR of Tri-trifluoroacetyl cyclam

Figure 2. 1H NMR of Tri-trifluoroacetyl cyclam

Figure 3. 19F NMR of Tri-trifluoroacetyl cyclam

PROCESS FOR PREPARATION OF N-1 PROTECTED N RING NITROGEN CONTAINING CYCLIC POLYAMINES AND PRODUCTS THEREOF

BACKGROUND OF THE INVENTION

1. Field of the Invention

The present invention relates to the area of selective protection of identical amino groups in cyclic polyamines, and preferably, relates to an improved process for preparing 1, 1'-[1,4-phenylenebis (methylene)]-bis1,4,8,11-tetraazacyclotetradecane.

2. Description of the Prior Art

J. Med. Chem, Vol. 38, No. 2, pgs. 366–378 (1995) is directed to the synthesis and anti-HIV activity of a series of novel phenylbis(methylene)-linked bis-tetraazamacrocyclic analogs, including 1,1'-[1,4-phenylenebis (methylene)]-bis1,4,8,11-tetraazacyclotetradecane. This compound and its analogs are prepared by: 1) forming the tritosylate of the tetraazamacrocycle; 2) reacting the protected tetraazamacrocycle with an organic dihalide, e.g., dibromo-p-xylene, in acetonitrile in the presence of a base such as potassium carbonate; and 3) de-protecting the bis-tetraazamacrocycle prepared in 2) employing freshly prepared sodium amalgam, concentrated sulfuric acid or an acetic acid/hydrobromic acid mixture to obtain the desired cyclam dimer in the form of a salt.

U.S. Pat. No. 5,047,527 is directed to a process for preparing a mono-functionalized (e.g., monoalkylated) cyclic tetraamine comprising: 1) reacting the unprotected macrocycle with chrominum hexacarbonyl to obtain a triprotected tetraazacycloalkane compound; 2) reacting the free amine group of the triprotected compound prepared in 1) with an organic halide to obtain a triprotected mono-functionalized tetraazacycloalkane compound; and 3) deprotecting the compound prepared in 2) by simple air oxidation to obtain the desired compound.

In addition, the reference discloses alternative methods of tri-protection of cyclic tetraamine employing boron and phosphorous derivatives. These tri-protected intermediates are used in the preparation of linked compounds, including the cyclam dimer 1,1'-[1,4-phenylenebis (methylene)]-bis1, 4,8,11-tetraazacyclotetradecane, by reacting with an organic dihalide in a molar ratio of 2:1, followed by deprotection.

Synthetic Communications, 28(15), pgs. 2903–2906, (1998) describes an improved method adopting the above-mentioned phosphorous protection, deprotection sequence to make 1,1'-[1,4-phenylenebis (methylene)]-bis1,4,8,11-tetraazacyclotetradecane.

U.S. Pat. No. 5,606,053 is directed to a process for preparing cyclam dimer 1,1'-[1,4-phenylenebis (methylene)] bis1,4,8,11-tetraazacyclotetradecane. The compound is prepared by: 1) tosylation of tetraamine starting material to obtain an acyclic ditosyl intermediate and an acyclic tritosyl intermediate; 2) separation of the two different tosylation product from step 1), e.g. the ditosyl tetraamine and the tritosyl tetraamine; 3) alkylation of the ditosyl tetraamine with dibromoxylene, followed by tosylation to make hexato-sylated acyclic cyclam dimer; 4) alkylation of the tritosyl tetraamine from 1); 5) cyclization of the compound prepared in steps 3) and 4), i.e., the bridged hexatosyl acyclic dimer, by reacting it with three equivalents of ethylene glycol ditosylate; 6) detosylation of the cyclized cyclam dimer by reacting with a mixture of hydrobromic acid and glacial acetic acid to obtain the product in the form of an HBr salt.

U.S. Pat. No. 5,801,281 is directed to an improved process for preparing the cyclam dimer 1,1'-[1,4-phenylenebis (methylene)]-bis1,4,8,11-tetraazacyclotetradecane. The compound is prepared by: 1) reacting the acyclic tetraamine with 3 equivalents of ethyl trifluoroacetate; 2) alkylation of the tri-protected acyclic tetraamine with 0.5 equivalents of dibromoxylene, to obtain the 1,4 phenylene bis-methylene bridged acyclic dimer; 3) hydrolysis to remove the six trifluoroacetyl groups of the compound prepared in step 2); 4) tosylation of the compound prepared in step 3) to obtain the hexatosylated bridged tetraamine dimer; 5) cyclization of the compound in step 4) with ethylene glycol ditosylate to obtain the hexatosylated cyclam dimer; 6) detosylation of the compound prepared in step 5) to obtain the cyclam dimer 1,1'-[1,4-phenylenebis (methylene)]-bis1,4,8,11-tetraazacyclotetradecane in the form of a salt using HBr/HOAc mixture.

U.S. Pat. No. 5,064,956 discloses a process for preparing mono-alkylated polyazamacrocycles by reacting unprotected macrocycle with an electrophile in an aprotic, relatively non-polar solvent in the absence of a base. No example resembling the synthesis of cyclam dimer was provided.

Although the current approaches to 1,1'-[1,4-phenylenebis (methylene)]-bis1,4,8,11-tetraazacyclotetradecane via tri-protection of cyclam or starting from acyclic tetraamine as demonstrated previously are suitable to prepare the compound (supra), they both suffer from the fact that the key step in each process is low yielding. The average yield of tri-protection reported is rarely over 50%. The macrocyclizations are also frequently suffering from lower yields. In addition, the deprotection of tosyl groups is time consuming and requires relatively harsh conditions.

It is known to those skilled in the art that the direct N-1 protection of N-ring nitrogen containing cyclic polyamines, where "N-1 protection" refers to the protection of all but one nitrogen in a cyclic polyamine containing N amines and N equals the number of protectable primary or secondary amines, e.g. cyclam and cyclen (N=4 in both cases), are generally problematic. Protecting groups such as tosyl, mesyl, Boc etc have been tested and vigorously optimized. Nevertheless, the drawbacks of these existing methods are obvious in several general aspects: 1) the low to moderate yield (frequently less than 50%) during the N-1 protection pursued due to the concurrent formation, with relatively great amount, of from N–M (M<N) to N substituted derivatives; 2) the difficulty in the isolation of the N-1 protected intermediate from the mixture; and 3) in several cases, such as tosyl, the harsh conditions required in the removal of these protecting groups at certain stage of the application.

In particular, the chemistry related to the tri-protection of tetraazamacrocycles such as 1,4,8,11-tetraazacyclotetradecane (cyclam), 1,4,7,10-tetraazacyclododecane (cyclen) and the di-protection of 1,4, 7-triazacyclononane are currently under active development in the field. It will be obvious to those skilled in the art that these N-1 protected cyclic polyamines are useful intermediates that will lead to, after necessary manipulation, mono-substituted cyclic amines. Hence these are key intermediates having great potential in the preparation of MRI diagnostic agents (U.S. Pat. No. 5,994,536; U.S. Pat. No. 5,919,431; U.S. Pat. No. 5,871,709; U.S. Pat. No. 5,410,043; U.S. Pat. No. 5,277,895; U.S. Pat. No. 5,132,409; U.S. Pat. No. 4,885,363.) or for the preparation of anti-HIV compounds (U.S. Pat. No. 5,583,131; U.S. Pat. No. 5,698,546; U.S. Pat.

No. 5,021,409; and U.S. Pat. No. 6,001,826), or for the preparation of compounds disclosed in PCT WO 2000/45814.

More recently, U.S. Pat. No. 5,705,637 discloses a process for preparing tri-benzylated macrocycles following a macrocyclization/amide reduction sequence. The three benzyl groups are removed eventually to afford mono-substituted cyclen.

For those skilled in the art it will also be obvious that the N-1 protected cyclic macrocyclic polyamines of the present invention are useful, after necessary additional protection deprotection steps, for the preparation of N-1 substituted cyclic polyamines.

Certain unique nitrogen protecting groups other than those described above have been reported and offer from low to excellent selectivity among primary and secondary amines and between two secondary amines.

Tetrahedron Letters Vol. 36. No. 20, pgs 3451–3452, (1995) reported reactions using ethyl trifluoroacetate to selectively protect primary amine in the presence of secondary amine in several linear polyamine compounds.

Tetrahedron Letters Vol. 36. No. 41, pgs 7357–7360, (1995) relates to examples using single equivalent ethyl trifluoroacetate to selectively protect di-primary amines and di-secondary amines. One case involving a six-membered diamine piperazine demonstrated a moderate selectivity of 5.8:1 when one equivalent of ethyl trifluoroacetate is used per equivalent of piperazine. It is noted that treatment of piperazine with excess ethyl trifluoroacetate readily produces more double (full) protected product, thus significantly reduced selectivity.

U.S. Pat. No. 6,080,785 relates to new mono-functionalized ethylenediaminetetraacetic acid, diethylenetriaminepentaacetic acid and triethylenetetraaminehexaacetic acid derivatives. A linear 1,4,7-triazaheptane was treated with 1.1 equivalents of ethyl trifluoroacetate and produced a mixture of monoamide and diamide at a ratio of 9:1. This mixture was carried further to the next step.

The present invention is based on the discovery that, when certain protecting agents are used to protect cyclic polyamines containing N ring nitrogen (N≧3) with each nitrogen being separated by 2 or more carbon atoms, the rate of reaction will slow down sharply once N-1 nitrogens are protected, even when all of the nitrogens in the cyclic polyamine are originally chemically equivalent. These controlled reactions thus afford, in an excellent yield, the important N-1 protected polyazamacrocycles at high selectivity.

SUMMARY OF THE INVENTION

The present invention relates, for example, to efficient high yielding N-1 protection of cyclic polyamines containing a total of N amine nitrogens, where the ring has from 9 to 20 ring members and N is from 3 to 6 amine nitrogens spaced by 2 or more carbon atoms, using fluroronated acid esters and other structurally related protecting agents (formula III). The resultant protected amines prepared by this method are useful intermediates for the preparation of selectively N-substituted protected cyclic polyamines. The protected selectively N-substituted cyclic polyamine is readily deprotected under mild conditions to form selectively N-substituted cyclic polyamines.

More particularly, the current invention discloses, inter alia, the high yielding tri-protection of 1,4,8,11-tetraazacyclotetradecane (cyclam), 1,4,7,10-tetraazacyclododecane (cyclen) and di-protection of 1,4,7-triazacyclononane using agents such as those represented by formula III.

In addition, the present invention provides an extremely efficient and economic process for preparing 1,1'-[1,4-phenylenebis (methylene)]-bis1,4,8,11-tetraazacyclotetradecane from cyclam, by using protecting groups such as, but not limited to, trifluoroacetyl, following a reaction sequence of tri-protection, alkylation and deprotection.

Other aspects of the invention are described throughout the specification and in particular the claims.

DETAILED DESCRIPTION OF THE INVENTION

Figure 1:
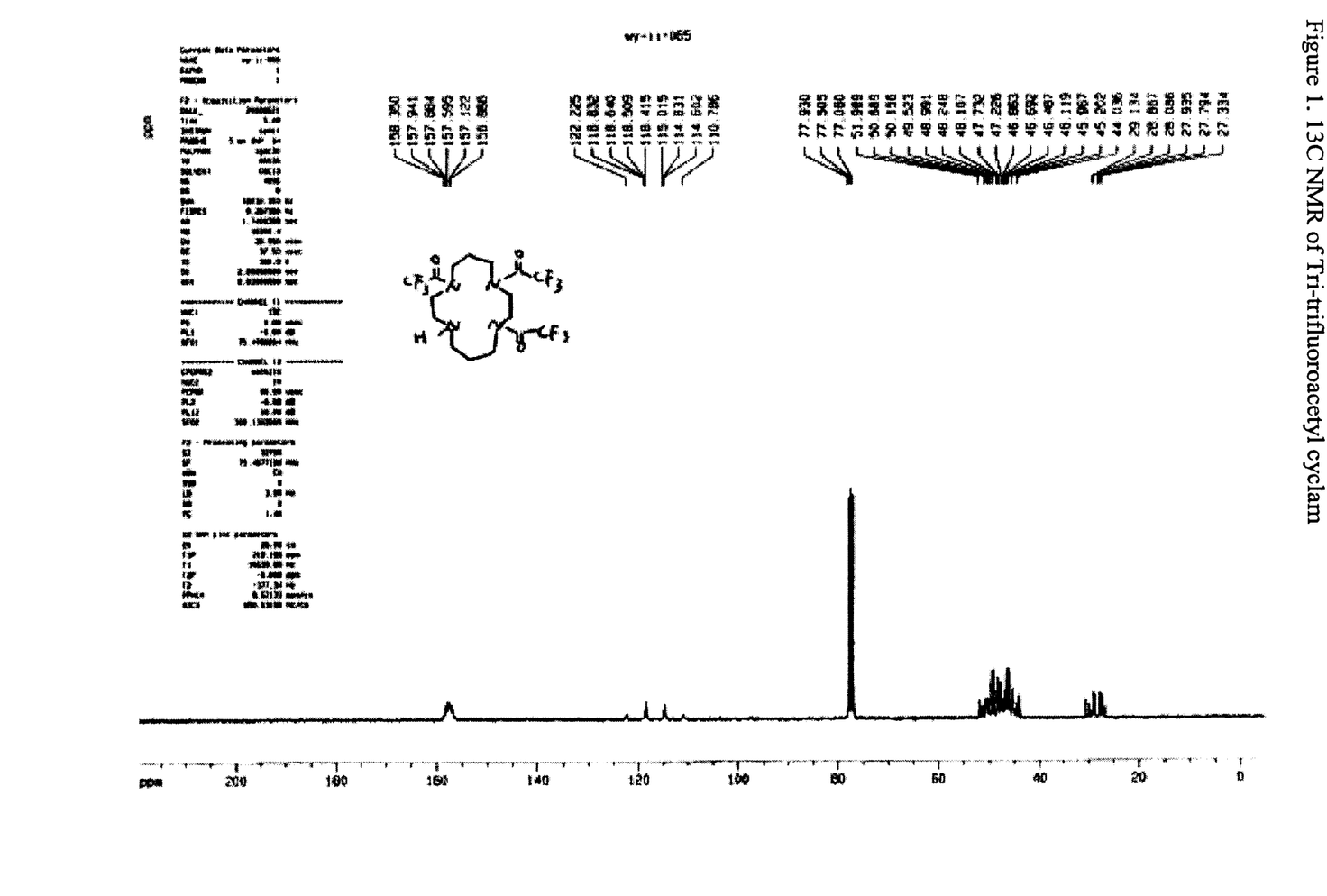
FIG. 1 depicts the $^{13}$C NMR of Tri-trifluoroacetyl cyclam.
Figure 2:
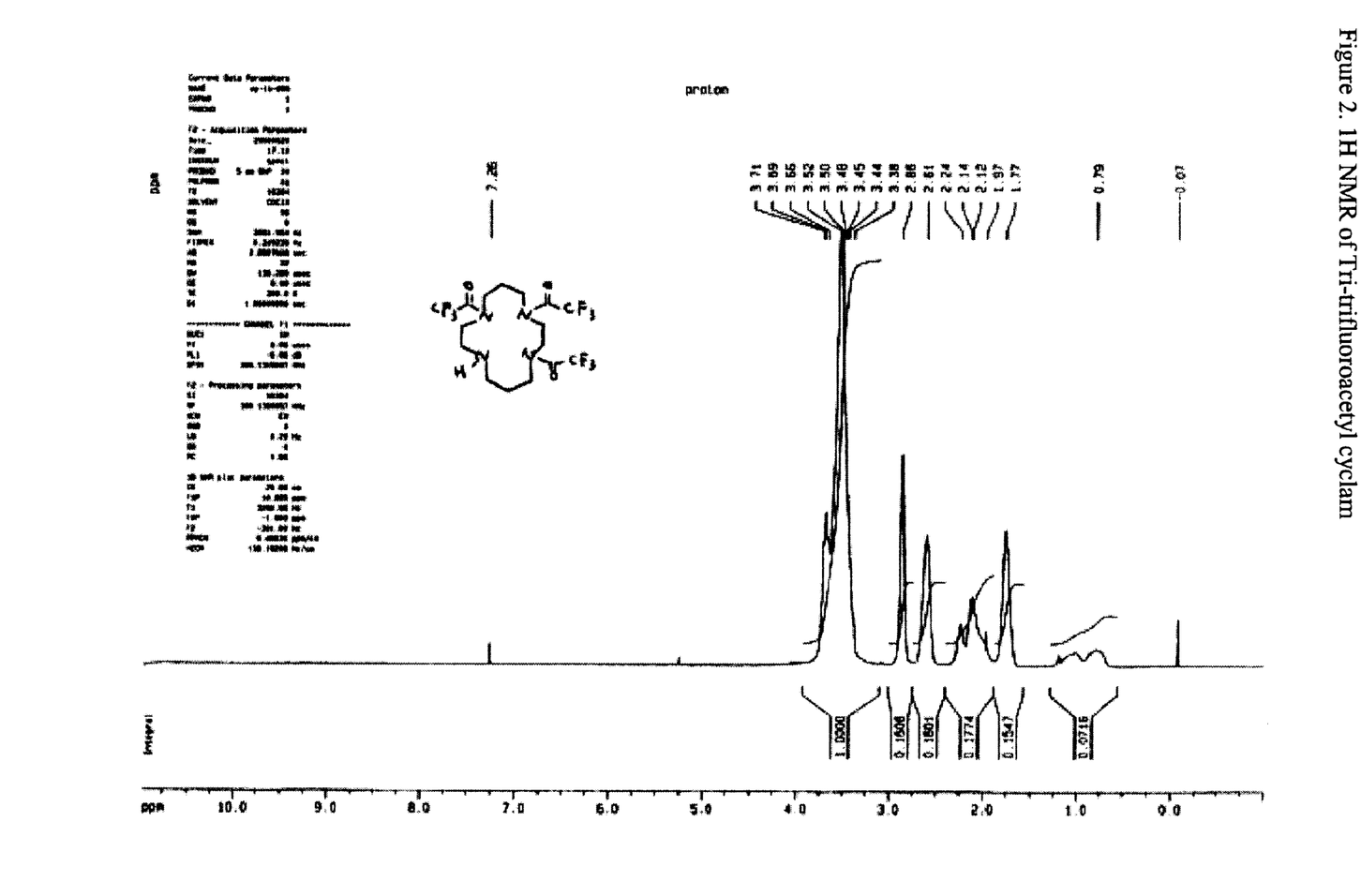
FIG. 2 depicts the $^{1}$H NMR of Tri-trifluoroacetyl cyclam.
Figure 3:
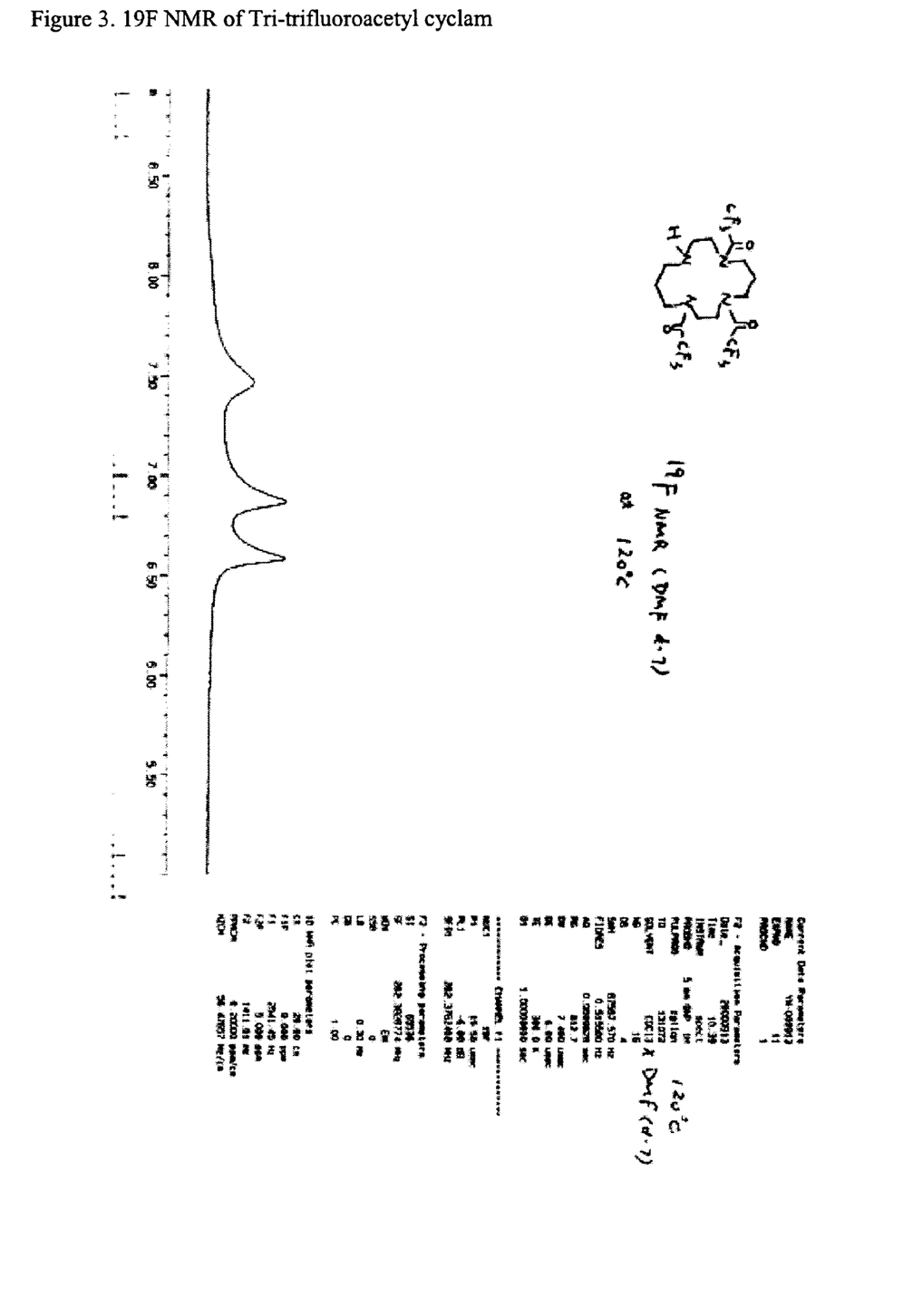
FIG. 3 depicts the $^{19}$F NMR of Tri-trifluoroacetyl cyclam.

The present invention relates to N-1 (i.e. all but one) protection of cyclic polyamines containing a total of N amine nitrogens on the ring system, where the ring has from 9 to 20 ring members and contains from 3 to 6 amine nitrogens spaced by 2 or more carbon atoms, using trifluoroacetyl and other structurally related protecting agents as represented by formula III.

III

Preferably, applicable cyclic polyamine may be represented by formulas I and II, where m and m' represent from 0 to 2 inclusive, preferably from 0 to 1 inclusive carbons; n, n' and n" represent from 1 to 3 inclusive, preferably from 1 to 2 inclusive carbons; m, m', n, n' and n" may be identical or different for any specific compound.

I

II

Even more preferable examples are cyclam (formula I, m=m'=n=n'=1), cyclen (formula I, m=m'=0, n=n'=1) and 1,4,7-triazacyclononane (formula II, n=n'=n"=1).

In another embodiment, one or more carbon atoms on the ring (formula I and II) may also be substituted with one or more atoms such as oxygen and/or sulfur.

The protecting agents are represented by formula III, where X is a fluoro-substituted, preferably perfluoro substituted aromatic, heteroaromatic, alkyl, alkenyl and/or alkynyl group, more preferably perfluoro substituted linear or branched alkyl group, most preferably perfluoro substituted saturated linear alkyl group containing 1–5 carbons, and further wherein X is preferably CyHpFz, wherein y is from 1 to 10 inclusive, p is from 0 to 20 inclusive, preferably 0 to 5, more preferably 0 to 2, and z is from 1 to 21 inclusive, preferably 1 to 9, more preferably 1 to 5; Lv is a moderately reactive nitrogen, oxygen, or sulfur containing leaving group such as, but not limited to, alkoxy, phenoxy, mercaptyl, imidazoyl, N-hydroxysuccinyl or other nitrogen or oxygen containing group preferably alkoxy containing 1–6 carbons, more preferably C1–C4. As would be well understood by someone skilled in the field, where u is the total number of rings and pi (double) bonds in the group, and t is the number of nitrogen atoms in the group, $z=1$ to $2y+1-2u+t$, and $p=2y+1-z-2u+t$. These and similar reagents can also be in the form of polymer-bound derivatives, such as those described by P. Suirskaya and L. Letnoff, J. Org. chem (1987) 52:1362–1364.

Compounds represented by formulas VIII and IX shown below are prepared, according to conditions detailed elsewhere herein, from reactions of I and II with III, respectively. In formulas VIII and IX, CyHpFz is as described above; m, m' are from 0 to 2 inclusive, n, n' and n" are from 1 to 3 inclusive carbons, and m, m', n, n' and n" may be identical or different for any specific compound.

VIII

IX

This N-1 protection is carried out using 1 to more than 100 equivalents, preferably N-1 to 3×N equivalents, most preferably N-1 to 2×N equivalents, of alkyl trifluoroacetate and/or other reagents with similar reactivity as defined by formula III per mole of cyclic polyamine where N=the number of ring nitrogens in the cyclic polyamine.

This N-1 protection reaction may be carried out in the presence of a diluting agent or a combination of diluting agents, such as: a C1–C12, preferably C1–C4, straight chain or branched chain alkanol, or a mixture of any other non-aqueous solvents with any alkanol described, including but not limited to methanol, ethanol, or low molecular weight (less than 5 carbon) alkanol such as butanol, or propanol; and/or pure alkyl trifluoroacetate, preferably methyl trifluoroacetate or ethyl trifluoroacetate, or other protecting agents adopted as defined by formula III.

Solvent or solvents used may contain certain levels of water without very serious product formation problem; however, it is preferable to exclude water. This may be accomplished by using additives that will sequester water.

The quantity of diluting agent employed may range from 0 to 100 liters per mole of the cyclic polyamine, preferably from 0 to 5 liter, most preferably from 2 to 3 liters, per mole of the cyclic polyamine.

Additives that will keep the reaction system acid free may be used such as carbonates, bicarbonates, phosphates, oxides, aluminates, aliphatic or aromatic amines, or polymer supported basic resins. Examples of amines includes aliphatic or aromatic amines that contain up to 24 carbons and preferably 3 to 12 carbons. Example of inorganic bases include alkali carbonates preferably sodium or potassium carbonate. The amount of this additive can range from 0 to a large excess, such as 0 to 10 equivalents, preferably 0 to 1 equivalents, more preferably 0.1 to 1 equivalents, per equivalent of the cyclic polyamine.

Alternatively, the N-1 protection operation may be advantageously carried out at temperatures from −78° C. to 120° C., preferably from −20° C. to 100° C., most preferably from 0° C. to 60° C.

The duration of the N-1 protection is generally on the order of 10 minutes to 72 hours, preferably from 1 hour to 24 hours, more preferably from 2 to 10 hours.

The product obtained from the reaction medium may be purified by methods such as, but not limited to, silica gel chromatography, recrystallization, acid wash and any other commonly practiced purification techniques. The product can also be isolated by treatment with salt forming acid in the form of amine salt, such as, but not limited to, the hydrogen chloride salt. Alternatively, the product may be used for further modification as crude without further purification.

The N-1 protected cyclic polyamine can be used in further reactions where the single unmasked amine nitrogen will take part. These reactions, which are known art of the field, will lead to mono-functionalized, N-1 differently protected cyclic polyamines. Commonly and conveniently, the N-1 protection groups such as trifluoroacetyl, may be removed, under various standard and mild conditions, to give mono-functionalized cyclic polyamines (T. W. Greene and P. G. M. Wuts, Protective Groups in Organic Synthesis, $3^{rd}$ edition, 1999, Wiley & Sons.). These are important intermediates and useful in the preparation of many known and potential cyclic polyamine based MRI chelating agents.

The aforementioned reactions may be used to synthesize compounds XIV and XVII as described herein, wherein CyHpFz is a fluoro-substituted alkyl, alkenyl, alkynyl, cycloalkyl, aromatic, or heteroaromatic group, wherein y is from 1 to 10, p is from 0 to 20, and z is from 1 to 21; wherein m and m' are from 0 to 2 and n, n' and n" are from 1 to 3; and wherein m, m', n, n' and n" may be the same or different; and wherein E is an alkyl, acyl, alkenyl, alkynl, hydroxyalkyl, cycloalkyl, aromatic, heteroaromatic, carboxamide, thiocarboxamide, carboxyl, phosphoryl or sulphato group.

XIV

In compounds XIV and XVII, E may also form a linker group, E″, which is attached to one macrocyclic nitrogen of each macrocyclic polyamine and is preferably a phenylene ring optionally substituted with an electron donating or withdrawing group consisting of alkyl, aryl, amino, alkoxy, hydroxy, halogen, carboxyl or carboxamido.

In a more general sense, the final compound may be represented by compound XX:

$$Q-E''-Q' \qquad XX$$

where Q and Q' may be the same or different and are macrocyclic polyamines represented by formulas I or II that are linked via E″.

For instance, when E is an aromatic ring, it may function to link two compound XIV groups together to form the compound according to formula XXI, wherein CyHpFz is a fluoro-substituted alkyl, alkenyl, alkynyl, cycloalkyl, aromatic, or heteroaromatic group, wherein y is from 1 to 10, p is from 0 to 20, and z is from 1 to 21; and wherein m and m' are from 0 to 2 and n and n' are from 1 to 3, and wherein m, m', n and n' may be the same or different, and wherein Ar is a phenylene ring, optionally substituted with an electron donating or withdrawing group such as alkyl, aryl, amino, alkoxy, hydroxy, halogen, carboxyl or carboxamido.

XXI

Preferably, linker Ar is formed from compound XI, wherein Lx and Lx' are the same or different and are moieties that can be displaced by an unprotected amine nitrogen. Preferably, Lx and Lx' are selected from Cl, Br, I, aryl sulfonate and alkyl sulfonate (e.g., 4-tolylsulfonate, methanesulfonate and trifluoromethane sulfonate).

XI

By way of example, the following description pertains to a process for preparing 1,1'[1,4-phenylenebis (methylene)]-bis 1,4,8,11-tetraazacyclotetradecane, which is a representative process according to the present invention, with the protecting step described above given by step 1.

Thus, the present invention is exemplified by the process for preparing 1,1'-[1,4-phenylenebis (methylene)]-bis1,4,8,11-tetraazacyclotetradecane via a three step sequence as depicted above. As shown, R in formula V and VI is the protecting moiety that is represented by formula III, where Lv is removed, preferably when X in Formula III is CyHpFz, and is a perfluoro substituted alkyl group containing 1 to 6 carbons, more preferably CyHpFz=CF$_3$.

Step 1

With respect to the individual steps, the first step involves the reaction of cyclam IV with a reagent represented by formula III. The reaction may use from 3 to 100 equivalents, preferably 3 to 10 equivalents of protecting agent III, in a non-aqueous solvent or a mixture of solvents suitable to dissolve the materials, preferably methanol, ethanol and/or other low molecular alcohol solvent or solvent mixture containing these polar solvents, at a temperature between −78° C. to 120° C., preferably between 20° C. to 60° C.

The reaction may take from 30 minutes to 72 hours, depending on the yield pursued, preferably from 2 hours to 10 hours. Other than the solvent system described above, suitable protecting agents such as depicted by formula III, preferably alkyl trifluoroacetate, more preferably methyl and/or ethyl trifluoroacetate can also serve as solvent for this reaction.

Additives that will keep the reaction system acid free may be used such as carbonates, bicarbonates, phosphates, oxides, aluminates, aliphatic or aromatic amines, or polymer supported basic resins. Examples of amines includes aliphatic or aromatic amines that contain up to 24 carbons and preferably 3 to 12 carbons. Example of inorganic bases include alkali carbonates preferably sodium or potassium carbonate. The amount of this additive can range from 0 to 10 equivalents, preferably from 0.1 to 1 equivalent, per equivalent of cyclam.

The product of Step 1, such as the tri-protected cyclam V, can be used as crude for the next step, or can be purified by silica gel column or using other common practice in the field such as, but not limited to, aqueous extraction work-up or recrystallization.

Step 2

The second step concerns functionalizing the remaining secondary amine from step 1 with a mono-reactive or di-reactive electrophile. For example, compound V obtained from step 1 can be alkylated using 1,4-dibromoxylene, 1,4-dichloroxylene, the ditosylate analogue or other similar alkylating agents. A wide range of organic solvents are suitable as diluting agents including acetonitrile, toluene, THF, DMF, 2-propanol and any other solvent or combination of solvents desirable for amine alkylation. The reaction may be carried out at a temperature from 20° C. to 150° C., preferably from 60° C. to 120° C. Further, any single or mixture of iodide anion containing compounds may be used as additives, including but not limited to KI, NaI, Bu$_4$NI, preferably KI. Additives that will keep the reaction system acid free may be used such as carbonates, bicarbonates, phosphates, oxides, aluminates, aliphatic or aromatic amines, or polymer supported basic resins. Examples of amines includes aliphatic or aromatic amines that contain up to 24 carbons and preferably 3 to 12 carbons. Example of inorganic bases include alkali carbonates preferably sodium or potassium carbonate.

Alternatively, reductive amination methods may be used. For example, terephthaldehyde may be reductively aminated with compound V using a reducing agent such as sodium cyanoborohydride or other borohydride reducing agents, or via catalytic hydrogenation. Additionally, the product from step 1 can also react with terephthaloyl chloride to obtain the corresponding diamide, followed by reduction to give the hexa-trifluoroacetyl cyclam dimer. The product VI from these alkylation reactions may be used as crude for the next step, or preferably, recrystallized from common solvents and/or mixture of solvents. These solvent systems include, but are not limited to, ethyl acetate, methanol, ethanol, methanol-water mixture etc.

In one embodiment of the invention, step two comprises reaction of compound VIII given above with the alkylating agent compound XI given above to form compound X.

Step 3

The third step of the process is deprotection (e.g. by saponification) of all the protecting groups in compound VI. Reagents that are useful for this saponification include, but are not limited to, alkoxides, hydroxides, amines, hydrazines, thiolates or other nucleophiles or reagents that generate nucleophiles such as metal carbonates in wet alcohols or water.

Alternatively, hydrolysis of the nitrogen protecting group in compound VI may be effected using acidic conditions such as those described in T. W. Greene and P. G. M. Wuts, Protective Groups in Organic Synthesis, 3$^{rd}$ edition, 1999, Wiley & Sons. A variety of other deprotection methods are also known to those skilled in the art. See T. W. Greene and P. G. M. Wuts, Protective Groups in Organic Synthesis, 3$^{rd}$ edition, 1999, Wiley & Sons. The final product VII can be obtained and purified by common methods such as, but not limited to, recrystallization, salt formation and chromatography.

In one embodiment of the present invention, step 2 is used to form the intermediate given by formula VIII above, which is reacted with a suitable electrophile selected from the group consisting of organic halides, tosylates, triflates, epoxides, thiocyanates and isocyanates to form a compound given by formula XIV above, wherein E is a functional group bonded to the nitrogen as described above. Then, step 3 consists of removing the (C=O)CyHpFz groups from the formula XIV compound using a method compatible with E to form a compound given by the formula XV.

In another embodiment, step 3 comprises removing the (C=O)CyHpFz groups from a compound given by formula XVII above using a method compatible with E to form a compound given by the formula XVIII.

XVIII

In yet another embodiment, when compound X as described above is deprotected in step three, this results in formation of compound XII.

XII

Step 4

Optional step 4 involves functionalizing all of the secondary amines released in the third step with an electrophile that includes but is not limited to an alkylating, acylating, sulphonylating or phosphorylating agent.

In one embodiment, step 4 comprises reacting the compound given by formula XV above with an electrophile, E', which is different from E, to form the compound according to the formula XVI

XVI wherein E' is selected from the group consisting of organic halide, tosylates, triflate, epoxide, thiocyanate, and isocyanate.

In another embodiment, step 4 comprises reacting the compound given by formula XVIII given above with an electrophile as described above to form the compound according to the formula XIX.

XIX

EXAMPLES

Having now generally described the invention, the same will be more readily understood by way of reference to the following examples which are provided and illustrated, and are not intended to be limiting of the present invention, unless specified.

Example 1

Preparation of 1,4,7-tris-(trifluoroacetyl)-1,4,7,10-tetraazacyclododecane Cyclen (2.13 g, 12.35 mmol) was dissolved in MeOH (20 mL). To the clear solution was added $NEt_3$ (1.70 mL, 12.35 mmol) in one portion, followed by slow addition of ethyl trifluoroacetate (7.35 mL, 61.76 mmol) during a period of 5 minutes. The reaction may be chilled to keep temperature under 25° C. Stirring was continued under $N_2$ for 15 hours. Volatiles were then removed under vacuum. The residue was dissolved in the minimum amount of $CH_2Cl_2$ (~2.0mL) and passed through a short silica gel pad, eluted with 100% EtOAc. The eluent was concentrated to give the product as a white semi solid (5.25 g, 92.5%). $^1H$ NMR (300 MHz, $CDCl_3$): δ3.90–3.76 (broad multiplet, 4 H, 3.68–3.20 (multiplet, 8 H), 3.10–2.65 (multiplet, 4 H), 1.40–1.25 (multiplet, 1 H). Mass $C_{14}H_{17}F_9N_4O_3$ requires C 36.53, H 3.72, N 12.17, O 10.43, found C 36.49, H 3.71, N 12.11, O 10.59.

Example 2

Preparation of 1,4-bis (trifluoroacetyl)-1,4,7-triazacyclononane 1,4,7-triazacyclononane (115.0 mg, 0.89 mmol) was dissolved in MeOH (2.0mL). To this clear solution was added $NEt_3$ (0.13 mL, 0.89 mmol) in one portion, followed by ethyl trifluoroacetate (0.43 mL, 13.56 mmol) during a period of 5 minutes. Stirring was continued under $N_2$ for 15 hours. Volatiles were then removed by rotavapor. The residue was dissolved in the minimum amount of $CH_2Cl_2$ (~2.0mL) and passed through a short silica gel pad, eluted with 100% EtOAc. The eluent was concentrated to give the product as a white solid (267.0 mg, 94%). $^1H$ NMR (300 MHz, $CDCl_3$): δ4.04–3.95 (multiplet, 2 H), 3.80–3.72 (multiplet, 2 H), 3.50–3.40 (multiplet, 4 H), 3.0–2.90 (multiplet, 4 H), 1.59 (singlet, 1 H). Mass calculated for $C_{10}H_{13}F_6N_3O_2$ 321.2, found M+1 322.1.

Example 3

Preparation of 1,4,8-tris (trifluoroacetyl)-1,4,8,11-tetraazacyclotetradecane Cyclam (7.53 g, 37.58 mmol) was dissolved in bench MeOH (30 mL). To this clear solution was added $NEt_3$ (5.20 mL, 37.58 mmol) in one portion, followed by portional addition of ethyl trifluoroacetate (18.0 mL, 150.3 mmol) during a period of 5 minutes. The reaction may be chilled to keep temperature under 25° C. Stirring was continued under $N_2$ for 5 h. Volatiles were then removed under vacuum. The residue was dissolved in minimum amount of $CH_2Cl_2$ (~2.0mL) and passed through a short silica gel pad (~25 g), eluted with 100% EtOAc. The eluent was concentrated to give the product as a white semi solid (17.05 g, 92.5%), $^1$H NMR (200 MHz, $CDCl_3$): δ3.85–3.25 (multiplet, 12 H), 2.80 (broad singlet, 2 H), 2.74–2.50 (broad singlet, 2H), 2.30–1.90 (multiplet, 2 H), 1.85–1.63 (multiplet, 2 H), 1.25–0.60 (multiplet, 1 H). $^{13}$C NMR (75.5 MHz, $CDCl_3$): δ158.74–157.31 (multiplet, C=O, muitiplets due to existence of conformers), 122.84–11.32 (quartet, $CF_3$, due to C—F coupling, $J_{C-F}$ ~264 Hz, further split due to existence of conformers), 51.2–46.2 (multiplet, $CH_2$ next to N), 29.4–27.8 (multiplet, $CH_2$); Mass of $C_{16}H_{21}F_9N_4O_3$ requires: C 39.35; H 4.33; N 11.47; O 9.83; found: C 39.19; H 4.36; N 11.33; O 10.04.

Example 4

Preparation of 1,1'-[1,4-phenylenebis (methylene)]-bis-tris-(trifluoroacetyl)-1,4,8,11-azatetradecane To a round bottom flask was charged 1,4,8-tris (trifluoroacetyl)-1,4,8,11-tetraazacyclotetradecane (3.70 g, 7.57 mmol) and anhydrous $CH_3CN$ (20 mL). The mixture was stirred at rt. until a solution was obtained (~10 min). To this solution was then added $K_2CO_3$ (98%, 1.57 g, 11.35 mmol), KI (62.8mg, 0.38 mmol) and Dichloro-xylene (663.0 mg, 3.78 mmol). The mixture was refluxed under $N_2$. TLC (1:1 EtOAc/Hexane) was used to monitor the reaction progress, which was completed after ~16 h. The mixture was cooled to rt. and filtered through a sintered glass filter to remove insoluble salt (washed with 20 mL $CH_3CN$). The solution was then concentrated to give a slightly yellowish solid. The solid was recrystallized using 4/1 $EtOH/H_2O$ to give the purified product (3.47 g, 85%) as an off white solid. $^1$H NMR (300 MHz, $CDCl_3$): δ7.25–7.06 (multiplet, 5 H), 3.80–3.20 (multiplet, 28 H), 2.75 (broad singlet, 4 H), 2.45–2.20 (multiplet, 8 H), 1.90–1.60 (multiplet, 4 H); $^{13}$C NMR (75.5 MHz, $CDCl_3$): δ155.6–154.5 (multiplet, C=O, multiplet due to conformers), 135.9–134.0 (multiplet, aromatic C), 127.9–126.7 (multiplet, aromatic C—H), 118.0 (quartet, $J_{C-F}$~287 Hz), 58.3–57.7 (multiplet), 55.0–52.0 (multiplet), 50.4–42.7 (multiplet due to conformers), 26.5–21.8 (multiplets due to conformers). Elemental analysis for $C_{40}H_{48}F_{18}N_8O_6$ calculated C 44.53, H 4.48, N 10.39, O 8.90, found C 44.46, H 4.40, N 10.26, O 9.11.

Example 5

Preparation of 1,1'-[1,4-phenylenebis (methylene)] bis1,4,8,11-tetraazacyclotetradecane, compound XII:

1,1'-[1,4-phenylenebis (methylene)]-bis-tris-(trifluoroacetyl)-1,4,8,11-azatetradecane (3.30 g, 3.05 mmol) was dissolved in MeOH (6.0 mL). $K_2CO_3$ (1.27 g, 9.1 mmol) was added in one portion. The suspension was heated at reflux for 3 h. Toluene (30 mL) was then added to the cooled mixture. MeOH was removed by forming an azeotrope with toluene. After all MeOH was removed, the hot toluene solution suspended with inorganic salt was filtered and concentrated to give AMD3100 free base (1.32 g, 86%) as a white solid. All characteristics of this product are in good agreement with an authentic sample prepared according to reported methods.

Example 6

Preparation of 1,4,7-triazacyclononane-1-acetamide

Bis-TFA 1,4,7-triazacyclononane (261.4 mg, 0.81 mmol) was dissolved in acetonitrile (5.0 mL), bromoacetamide (168.1 mg, 1.22 mmol) and $K_2CO_3$ (225.0 mg, 1.62 mmol) were added sequentially. The mixture was refluxed for 15 hours. Filtration and chromatography of the residue after removal of all volatiles gave the desired product as an oil (214.0 mg, 70%).

Example 7

Preparation of 1,4,8-tris (pentafluoropropionyl)-1,4,8,11-tetraazacyclotetradecane Cyclam (618.9 mg, 3.08 mmol) was dissolved in methanol (5.0 mL). $NEt_3$ (0.43 ml, 3.08 mmol) and methyl pentafluoropropionate (2.0 mL, 15.44 mmol) were added sequentially. The reaction was continued at room temperature for 15 h. After removal of volatiles, the residue was chromatographed to give 1,4,8-tris (pentafluoropropionyl)-1,4,8,11-tetraazacyclotetradecane (660.0 mg, 34%) as a white foam. $^1$H NMR (CDCl$_3$, 200MHz): δ4.0–3.28 (multiplet, 10 H), 2.86 (broad multiplet, 2 H), 2.64–2.59 (multiplet, 2 H), 2.48–1.99 (multiplet, 2 H), 1.8–1.7 (multiplet, 2H), 1.1 (s, 1 H); $^{13}$C NMR (75.5 MHz, CDCl$_3$): δ159.4–157.7 (multiplet, C=O), 123.9–111.8 (triplet of quartet, $J_{C-F}$=249 Hz, 34 Hz, $CF_3CF_2$), 112.6–104.6 (multiplet of triplet, $J_{C-F}$=308 Hz, $CF_2CF_3$), 50.3–44.4 (multiplet, $CH_2$ next to N), 28.9–27.8 (multiplet, $CH_2$); $C_{19}H_{21}N_4F_{15}O_3$ requires: C 35.75, H 3.32, N 8.78, O 7.52, found C 35.81, H 3.37, N 8.55, O 7.74.

Example 8

Preparation of urea derivative of 1,4,7-tris (trifluoroacetyl)-1,4,7,10-tetraazacyclododecane (Ph = Phenol)

1,4,7-tris (trifluoroacetyl)-1,4,7,10-tetraazacyclododecane (303.5 mg, 0.658 mmol) was dissolved in $CH_2Cl_2$ (5.0 mL). Phenyl isocyanate (0.14 mL, 1.32 mmol) was added in one portion. The reaction was continued at room temperature for 15 hours. After removal of all volatiles, the residue was chromatographed to give the desired urea derivative (301.0 mg, 79%). $^1$H NMR (CDCl$_3$, 200 MHz): δ7.38–7.26 (multiplet, 5H), 7.08–7.03 (multiplet, 1H), 4.03–3.28 (multiplet, 16 H); MS calculated for $C_{21}H_{22}N_5F_9O_4$ 579.4, found M+Na: 602.5.

Example 9

Preparation of mono-Cbz-tris-(trifluoroacetyl) cyclam (Ph = Phenol)

Tri-TFA cyclam was dissolved in $CH_2Cl_2$ (10 mL) at room temperature. $Na_2CO_3$ (566 mg, 5.34 mmol) was added in one portion, followed by slow addition of Cbz chloride. The reaction was monitored by TLC (1:1 ethyl acetate: hexane). The reaction was stopped after 15 hours. Usual work up followed by column chromatography using silica gel afforded the product (1.30 g, 94%) as a white foam. $^1$H NMR (CDCl$_3$, 200 MHz): δ7.31 (broad multiplet, 5 H), 5.02 (s, 2 H), 3.54–3.10 (multiplet, 16 H), 2.04–1.54 (multiplet, 4 H); Mass for $C_{24}H_{27}F_9N_4O_4$, calculated: 622.5, found M+1 623.2.

Example 10

Preparation of mono-tosyl-tris-(trifluoroacetyl) cyclam (Ts = toluenesulfonyl, or tosyl)

Tri-TFA cyclam (3.31 g, 6.77 mmol) was dissolved in CH$_2$Cl$_2$ (30 mL). Triethyl amine (1.40 mL, 8.12 mmol) was added in one portion. The solution was cooled in an ice water bath. TsCl (1.55 g, 8.12 mmol) was added in small portions during a period of 5 minutes. The reaction was continued at room temperature for 8 hours. Usual work up and column chromatography afforded the desired the product (3.47 g, 80%). $^1$H NMR (300 MHz, CDCl$_3$): δ7.5–7.48 (multiplet, 2H), 7.26–7.20 (multiplet, 2 H), 3.67–3.30 (multiplet, 12 H), 3.21 (broad multiplet, 2 H), 2.95 (broad multiplet, 2 H), 2.32 (s, 3 H), 2.20–1.70 (multiplet, 4 H). $^{13}$C NMR (75.5 MHz, CDCl$_3$): δ158.4–156.4 (multiplet, C=O), 144.8–144.7 ( two singlet due to conformers), 134.2–133.8 ( four singlet due to ring conformers), 133.8, 127.7–127.5 ( two singlet due to conformers), 122.3–110.8 (four singlet, due to C—F coupling, J$_{C-F}$~287 Hz), 51.8–45.0 (multiplet due to conformers), 28.4–27.2 (multiplet due to conformers), 21.6.

Example 11

Preparation of mono-Cbz cyclam

(Ph = Phenol)

Mono-Cbz-tris-(trifluoroacetyl) cyclam (4.0 g, 6.4 mmol) was dissolved in bench MeOH (50 mL). K$_2$CO$_3$ (2.0 g, 14.5 mmol) was added in one portion. The mixture was refluxed for 15 h. Most of the volatiles was removed under vacuum and the residue was taken into CHCl$_3$ (100 mL). The solid was filtered off and the solution was concentrated to give mono-Cbz cyclam (1.82 g, 85%). $^1$H NMR (CDCl$_3$, 200 MHz): δ7.21–7.14 (multiplet, 5 H), 4.98 (singlet, 2 H), 3.33 (triplet, 2 H), 3.26 (triplet, 2 H), 2.67 (triplet, 2 H), 2.60–2.51 (multiplet, 10 H), 1.68 (broad singlet, 3 H), 1.68–1.49 (multiplet, 4 H).

Citation of documents herein is not intended as an admission that any of the document is prior art. All statements as to the date or representation as to the contents of these documents is based on the information available to the applicants and does not constitute any admission of the correctness of the dates or contents of these documents. Further, all publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the same or any related fields are intended to be within the scope of the following claims.

What is claimed is:

1. A compound according to formula VIII, wherein CyHpFz is a fluoro-substituted alkyl, alkenyl, alkynyl, cycloalkyl, aromatic, or heteroaromatic group, wherein y is from 1 to 10, p is from 0 to 20, and z is from 1 to 21; and wherein m and m' are from 0 to 2 and n and n' are from 1 to 3; and wherein m, m', n and n' may be the same or different;

VIII

2. A compound according to formula IX, wherein CyHpFz is a fluoro-substituted alkyl, alkenyl, alkynyl, cycloalkyl, aromatic, or heteroaromatic group, wherein y is from 1 to 10, p is from 0 to 20, and z is from 1 to 21; and wherein n, n' and n" are from 1 to 3; and wherein n, n' and n" may be the same or different;

3. A compound according to formula XIV, wherein CyHpFz is a fluoro-substituted alkyl, alkenyl, alkynyl, cycloalkyl, aromatic, or heteroaromatic group, wherein y is from 1 to 10, p is from 0 to 20, and z is from 1 to 21; wherein m and m' are from 0 to 2 and n and n' are from 1 to 3; and wherein m, m', n and n' may be the same or different; and wherein E is an alkyl, acyl, alkenyl, alkynl, hydroxyalkyl, cycloalkyl, aromatic, heteroaromatic, carboxamide, thiocarboxamide, carboxyl, phosphoryl or sulphato group;

XIV

4. A compound according to formula XVII, wherein CyHpFz is a fluoro-substituted alkyl, alkenyl, alkynyl, cycloalkyl, aromatic, or heteroaromatic group, wherein y is from 1 to 10, p is from 0 to 20, and z is from 1 to 21; wherein n, n' and n" are from 1 to 3, and wherein n, n' and n" may be the same or different; and wherein E is an alkyl, acyl, alkenyl, alkynl, hydroxyalkyl, cycloalkyl, aromatic, heteroaromatic, carboxamide, thiocarboxamide, carboxyl, phosphoryl or sulphato group;

XVII

5. A compound according to formula XXI wherein CyHpFz is a fluoro-substituted alkyl, alkenyl, alkynyl, cycloalkyl, aromatic, or heteroaromatic group, wherein y is from 1 to 10, p is from 0 to 20, and z is from 1 to 21; and wherein m and m' are from 0 to 2 and n and n' are from 1 to 3; and wherein m, m', n and n' may be the same or different; and wherein Ar is a phenylene ring optionally substituted with an electron donating or withdrawing group selected from the group consisting of alkyl, aryl, amino, alkoxy, hydroxy, halogen, caboxyl and carboxamido;

XXI

6. The compound according to claim 1 wherein m=m'=n=n'=1; y=1; p=0; and z=3.
7. The compound according to claim 2 wherein m=m'=n=n'=1; y=1; p=0; and z=3.
8. The compound according to claim 3 wherein m=m'=n=n'=1; y=1; p=0; and z=3.
9. The compound according to claim 4 wherein m=m'=n=n'=1; y=1; p=0; and z=3.
10. The compound according to claim 5 wherein m=m'=n=n'=1; y=1; p=0; and z=3.
11. The compound according to claim 10, wherein Ar is an optionally substituted phenylene ring.
12. The compound according to claim 10 having the structure:

13. A process for making compounds of formulas XV, XVIII, or XX wherein n, n' and n" are from 1 to 3; m and m' are from 0 to 2, and wherein n, n', n", m and m' may be the same or different; and wherein E is alkyl, acyl, alkenyl, alkynl, hydroxyalkyl, cycloalkyl, aromatic, heteroaromatic, carboxamide, carboxyl phosphoryl or sulphato groups; and wherein Q and Q' are the same or different and are macrocyclic polyamines represented by formulas I or II that are linked by E", wherein E" is a linking group as defined by E attached to one macrocyclic nitrogen of each macrocyclic polyamine, said process comprising the steps of:

1) selectively acylating N-1 cyclic amines in a reaction mixture, wherein N=the number of secondary amines contained within the macrocycle, with a fluoro-substituted acylating agent of formula III, wherein X is a substituted aromatic, heteroaromatic, alkyl, alkenyl or alkynyl group; and wherein Lv is a N, O or S-containing leaving group;

2) functionalizing the remaining secondary amine with a mono-reactive electrophile to form compounds of formulas XV or XVIII or a di-reactive electrophile to form compound XX in step 3; and

3) removing the acyl groups added in step 1 to form compounds of formula XV, XVIII, or XX.

XV

XVIII

XX

14. The process according to claim 13, wherein X in formula III of step 1 is CyHpFz, and wherein p=0.

15. The process according to claim 14, wherein CyHpFz is a saturated linear alkyl group wherein y=1 to 5.

16. The process according to claim 13, wherein Lv in formula III is an alkoxyl or a phenoxyl.

17. The process according to claim 16, wherein Lv in formula III is a C1–C4 alkoxyl group.

18. The process according to claim 13, wherein step 1 comprises adding 1 to 10 equivalents of unreactive amines containing from 1 to 15 carbons to the reaction mixture.

19. The process according to claim 13, wherein step 1 comprises adding a diluting agent to the reaction mixture, wherein the diluting agent comprises a C1 to C12 straight chain or branched alkanol.

20. The process according to claim 13, wherein step 1 comprises adding 2 to 100 equivalents of ethyl trifluoroacetate, and wherein step 1 is carried out in the presence of methanol at a temperature from 10° C.–40° C. for a period of between 1 hour and 24 hours.

21. The process according to claim 13, wherein step 1 results in formation of a compound given by formula VIII, where m=m'=n=n'=1; and wherein the di-reactive electrophile of step 2 is a 1,4-phenylene alkylating agent of formula XI; and wherein step 3 results in formation of a compound of formula X.

22. The process according to claim 21, wherein Lx and Lx' of formula XI are selected from the group consisting of: Cl, Br, I, alkyl sulfonate and aryl sulfonate.

23. The process according to claim 21, wherein the alkylating agent is 1,4 dichloroxylene or 1,4 dibromoxylene.

24. The process according to claim 21, wherein step 2 comprises addition of an iodide anion-containing compound.

25. The process according to claim 21, wherein step 2 comprises addition of a metal carbonate as the base.

26. The process according to claim 21, wherein step 2 comprises addition of unreactive organic amines containing from 3 to 9 carbons.

27. The process according to claim 21, wherein the alkylating agent is dissolved in a solvent selected from the group consisting of acetonitrile, alkanol with from 1 to 12 carbons, cyclic ether, toluene, N,N-dimethyl formide and N,N-dimethyl acetamide or mixtures thereof.

28. The process according to claim 21, wherein step 2, the alkylating agent is dichloroxylene, and is present in 0.3 to 0.7 equivalents and 0.015 to 2 equivalents of KI is added, and 0.5 to 50 equivalents of $K_2CO_3$ is added, and the reaction is carried out in the presence of acetonitrile at between 40° C. for a period of between 4 hours and 72 hours.

29. The process according to claim 13, wherein step 3 comprises removing the aryl groups from compound X with a deprotecting agent.

30. The process according to claim 29, wherein the deprotecting agent is a metal carbonate.

31. The process according to claim 29, wherein the deprotecting agent is a metal hydroxide.

32. The process according to claim 29, wherein the deprotecting agent is dissolved in a solvent selected from the group consisting of a polar organic solvent, water, and a mixture of a polar organic solvent and water.

33. The process according to claim 29, wherein the deprotecting agent is an acid or mixture of acids.

34. The process according to claim 29, wherein the deprotecting agent is ammonia in any form or an organic amine containing from 1 to 20 carbons.

35. The process according to claim 29, wherein the deprotecting agent is a sulphur containing compound.

36. The process according to claim 13, wherein step 2 comprises reacting a compound given by formula VIII with an electrophile selected from the group consisting of organic halides, tosylates, triflates, epoxides, thiocyanates and isocyanates to form a compound given by formula XIV.

XIV

37. The process according to claim 36, wherein step 3 comprises removing the (C=O)CyHpFz groups to form a compound given by formula XV;

XV

38. The process according to claim 13, further comprising step 4 of reacting the compound formed in step 3 with an electrophile, E', which is different from E.

39. The process according to claim 38, wherein the electrophile is selected from the group consisting of organic halide, tosylates, triflate, epoxide, thiocyanate, and isocyanate.

40. The process according to claim 39, wherein step 3 results in formation of a compound given by formula XV, and wherein step 4 results in formation of a compound given by formula XVI;

XVI

41. The process according to claim 13, wherein step 2 comprises reacting a compound given by formula IX with an electrophile to form a compound given by formula XVII;

XVII

42. The process according to claim 41, wherein the electrophile is selected from the group consisting of organic halides, tosylates, triflates, epoxides, thiocyanates, and isocyanates.

43. The process according to claim 13, wherein step 3 comprises removing the (C=O)CyHpFz groups to form a compound given by the formula XVIII;

XVIII

44. The process according to claim 38, wherein step 4 comprises reacting the compound given by formula XVIII with an electrophile to form the compound given by formula XIX.

XIX

45. The process according to claim 44, wherein the electrophile is selected from the group consisting of organic halides, tosylates, triflates, epoxides, thiocyanates, and isocyanates.

* * * * *